US011534425B2

(12) United States Patent
Jackson et al.

(10) Patent No.: US 11,534,425 B2
(45) Date of Patent: Dec. 27, 2022

(54) COMPOUNDS FOR THE TREATMENT OF ACUTE ORGAN INJURY

(71) Applicant: UNIVERSITY OF PITTSBURGH—OF THE COMMONWEALTH SYSTEM OF HIGHER EDUCATION, Pittsburgh, PA (US)

(72) Inventors: Travis C. Jackson, Pittsburgh, PA (US); Patrick M. Kochanek, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 174 days.

(21) Appl. No.: 16/584,314

(22) Filed: Sep. 26, 2019

(65) Prior Publication Data

US 2020/0093798 A1  Mar. 26, 2020

Related U.S. Application Data

(60) Provisional application No. 62/736,554, filed on Sep. 26, 2018.

(51) Int. Cl.
| | | |
|---|---|---|
| *A61K 31/416* | (2006.01) |
| *A61K 31/404* | (2006.01) |
| *A61P 25/00* | (2006.01) |
| *A61K 31/423* | (2006.01) |
| *A61K 31/381* | (2006.01) |
| *A61K 31/47* | (2006.01) |
| *A61K 31/505* | (2006.01) |
| *A61K 31/498* | (2006.01) |
| *A61K 31/428* | (2006.01) |

(52) U.S. Cl.
CPC .......... *A61K 31/416* (2013.01); *A61K 31/381* (2013.01); *A61K 31/404* (2013.01); *A61K 31/423* (2013.01); *A61K 31/428* (2013.01); *A61K 31/47* (2013.01); *A61K 31/498* (2013.01); *A61K 31/505* (2013.01); *A61P 25/00* (2018.01)

(58) Field of Classification Search
CPC .. A61K 31/381; A61K 31/404; A61K 31/416; A61K 31/423; A61K 31/47; A61K 31/505; A61K 31/498; A61K 31/428; A61P 25/00
See application file for complete search history.

(56) References Cited

U.S. PATENT DOCUMENTS 6,358,696 B1 * 3/2002 McBurney ........... A61K 31/155
                                                   435/7.2

OTHER PUBLICATIONS

Jackson, et al., "Pharmacological Inhibition of Pleckstrin Homology Domain Leucine-Rich Repeat Protein Phosphatase Is Neuroprotective: Differential Effects on Astrocytes", J Pharmacol Exp Ther 347:516-528, Nov. 2013.
Sierecki, et al., "Discovery of Small Molecule Inhibitors of the PH Domain Leucine-Rich Repeat Protein Phosphatase (PHLPP) by Chemical and Virtual Screening", J. Med. Chem. 2010, 53, 6899-6911.
Gao, Tianyan, Frank Furnari, and Alexandra C. Newton. "PHLPP: a phosphatase that directly dephosphorylates Akt, promotes apoptosis, and suppresses tumor growth." Molecular cell 18.1 (2005): 13-24.
Brognard, John, et al. "PHLPP and a second isoform, PHLPP2, differentially attenuate the amplitude of Akt signaling by regulating distinct Akt isoforms." Molecular cell 25.6 (2007): 917-931.
Chen, Bo, et al. "PHLPP1 gene deletion protects the brain from ischemic injury." Journal of Cerebral Blood Flow & Metabolism 33.2 (2013): 196-204.
University of Pittsburgh, Department of Critical Care Medicine Annual Report FY2017, 143 pages.

* cited by examiner

*Primary Examiner* — Barbara P Badio
(74) *Attorney, Agent, or Firm* — Meunier Carlin & Curfman LLC (57) ABSTRACT

Disclosed herein are novel compounds and methods for the treatment of acute organ injury, including injuries resulting from ischemic events. The compounds may be used to treat organ including the brain, heart, or kidney, which have injured as a result of events such as stroke, cardiac arrest, traumatic brain injury, hemorrhagic shock, or subarachnoid hemorrhage.

8 Claims, 4 Drawing Sheets

COMPOUNDS FOR THE TREATMENT OF ACUTE ORGAN INJURY

CROSS-REFERENCE TO RELATED APPLICATION

This application claims the benefit of U.S. Provisional Application 62/736,554, filed Sep. 26, 2018, the contents of which are hereby incorporated in its entirety.

STATEMENT OF GOVERNMENT SUPPORT

This invention was made with government support under NS088145 awarded by the National Institutes of Health. The government has certain rights in this invention.

FIELD OF THE INVENTION

The invention is directed to methods of treating acute organ injury, including injuries to the central nervous system, cardiovascular system, and renal system.

SUMMARY

Disclosed herein are neuroprotective compounds useful for treating organ injury relating to ischemic events.

The details of one or more embodiments are set forth in the descriptions below. Other features, objects, and advantages will be apparent from the description and from the claims.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The term "alkyl" as used herein is a branched or unbranched hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. An alkyl group which contains no double or triple carbon-carbon bonds is designated a saturated alkyl group, whereas an alkyl group having one or more such bonds is designated an unsaturated alkyl group. Unsaturated alkyl groups having a double bond can be designated alkenyl groups, and unsaturated alkyl groups having a triple bond can be designated alkynyl groups. Unless specified to the contrary, the term alkyl embraces both saturated and unsaturated groups.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is replaced with a heteroatom such as, but not limited to, nitrogen, oxygen, sulfur, selenium or phosphorus. The cycloalkyl group and heterocycloalkyl group can be substituted or unsubstituted. Unless stated otherwise, the terms "cycloalkyl" and "heterocycloalkyl" contemplate both substituted and unsubstituted cycloalkyl and heterocycloalkyl groups. The cycloalkyl group and heterocycloalkyl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. A cycloalkyl group which contains no double or triple carbon-carbon bonds is designated a saturated cycloalkyl group, whereas an cycloalkyl group having one or more such bonds (yet is still not aromatic) is designated an unsaturated cycloalkyl group. Unless specified to the contrary, the term cycloalkyl embraces both saturated and unsaturated, non-aromatic, ring systems.

The term "aryl" as used herein is an aromatic ring composed of carbon atoms. Examples of aryl groups include, but are not limited to, phenyl and naphthyl, etc. The term "heteroaryl" is an aryl group as defined above where at least one of the carbon atoms of the ring is replaced with a heteroatom such as, but not limited to, nitrogen, oxygen, sulfur, selenium or phosphorus. The aryl group and heteroaryl group can be substituted or unsubstituted. Unless stated otherwise, the terms "aryl" and "heteroaryl" contemplate both substituted and unsubstituted aryl and heteroaryl groups. The aryl group and heteroaryl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol.

Exemplary heteroaryl and heterocyclyl rings include: benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyL cirrnolinyl, decahydroquinolinyl, 2H,6H~1,5,2-dithiazinyl, dihydrofuro[2,3b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl as defined above. "Alkoxy" also includes polymers of alkoxy groups as just described; that is, an alkoxy can be a polyether such as $—OA^1-OA^2$ or $—OA^1—(OA^2)_a-OA^3$, where "a" is an integer of from 1 to 200 and $A^1$, $A^2$, and $A^3$ are alkyl groups.

The terms "cycloalkoxy," "heterocycloalkoxy," "cycloalkoxy," "aryloxy," and "heteroaryloxy" have the aforementioned meanings for alkyl, cycloalkyl, heterocycloalkyl, aryl and heteroaryl, further providing said group is connected via an oxygen atom.

As used herein, the term "null," when referring to a possible identity of a chemical moiety, indicates that the group is absent, and the two adjacent groups are directly bond to one another. By way of example, for a genus having the formula $CH_3$-X-$CH_3$, if X is null, then the resulting compound has the formula $CH_3—CH_3$.

As used herein, two atoms connected via the symbol ∥ may be connected via a single or double bond.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless specifically stated, a substituent that is said to be "substituted" is meant that the substituent can be substituted with one or more of the following: alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. In a specific example, groups that are said to be substituted are substituted with a protic group, which is a group that can be protonated or deprotonated, depending on the pH.

Unless specified otherwise, the term "patient" refers to any mammalian animal, including but not limited to, humans.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Disclosed herein are compounds that can be used to reduce organ injury resulting from an ischemic event, the compounds having the formula:

or a pharmaceutically acceptable salt thereof,
wherein
$Ar^1$ comprises an aryl or heteroaryl group;
$L^1$ is selected from null and $C_{1-6}$alkyl;
$R^{x1}$ is selected from hydrogen, $C_{1-6}$alkyl;
X is O, $NR^N$ or S; wherein $R^N$ is selected from $R^{N'}$, $OR^{N'}$, $N(R^{N'})_2$, $SO_2R^{N'}$, $SO_2N(R^{N'})_2$, $C(O)R^{N'}$; $C(O)OR^{N'}$, $OC(O)R^{N'}$; $C(O)N(R^{N'})_2$, $N(R^{N'})C(O)R^{N'}$, $OC(O)N(R^{N'})_2$, $N(R^{N'})C(O)N(R^{N'})_2$, wherein $R^{N'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
$R^{x2}$ is selected from hydrogen, $C_{1-6}$alkyl;
$L^2$ is selected from null and $C_{1-6}$alkyl;
$Ar^2$ is selected from an aryl and heteroaryl group;
wherein any two or more of $Ar^1$, $L^1$, $R^{x1}$, $R^N$, $R^{x2}$, $L^2$ and $Ar^2$ may together form a ring.

In some instances, $Ar^1$ can be an aryl or heterocycle having the formula:

wherein $X^{1a}$ is selected from $-N=CR^{x1a1}-$; $-CR^{x1a1}=N-$; O, S, and $NR^{x1a}$;
$X^{1b}$ is selected from N, $CR^{x1b}$, $-N=CR^{x1b1}-$; and $-CR^{x1b1}=CR^{x1b2}-$;
$X^{1c}$ is selected from N, $CR^{x1c}$, $-CR^{x1c1}=CR^{x1c2}-$;
wherein $R^{1a}$ is selected from $L^1$, F, Cl, Br, I, $NO_2$, CN, $R^{1a'}$, $OR^{1a'}$, $N(R^{1a'})_2$, $SO_2R^{1a'}$, $SO_2N(R^{1a'})_2$, $C(O)R^{1a'}$; $C(O)OR^{1a'}$, $OC(O)R^{1a'}$; $C(O)N(R^{1a'})_2$, $N(R^{1a'})C(O)R^{1a'}$, $OC(O)N(R^{1a'})_2$, $N(R^{1a'})C(O)N(R^{1a'})_2$, wherein $R^{1a'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{1b}$ is selected from $L^1$, $R^{1b'}$, $OR^{1b'}$, $N(R^{1b'})_2$, $SO_2R^{1b'}$, $SO_2N(R^{1b'})_2$, $C(O)R^{1b'}$; $C(O)OR^{1b'}$, $OC(O)R^{1b'}$; $C(O)N(R^{1b'})_2$, $N(R^{1b'})C(O)R^{1b'}$, $OC(O)N(R^{1b'})_2$, $N(R^{1b'})C(O)N(R^{1b'})_2$, wherein $R^{1b'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{1c}$ is selected from $L^1$, $R^{1c'}$, $OR^{1c'}$, $N(R^{1c'})_2$, $SO_2R^{1c'}$, $SO_2N(R^{1c'})_2$, $C(O)R^{1c'}$; $C(O)OR^{1c'}$, $OC(O)R^{1c'}$; $C(O)N(R^{1c'})_2$, $N(R^{1c'})C(O)R^{1c'}$, $OC(O)N(R^{1c'})_2$, $N(R^{1c'})C(O)N(R^{1c'})_2$, wherein $R^{1c'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{1d}$ is selected from $L^1$, $R^{1d'}$, $OR^{1d'}$, $N(R^{1d'})_2$, $SO_2R^{1d'}$, $SO_2N(R^{1d'})_2$, $C(O)R^{1d'}$; $C(O)OR^{1d'}$, $OC(O)R^{1d'}$; $C(O)N(R^{1d'})_2$, $N(R^{1d'})C(O)R^{1d'}$, $OC(O)N(R^{1d'})_2$, $N(R^{1d'})C(O)N(R^{1d'})_2$, wherein $R^{1d'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{x1a}$ is selected from $L^1$, $R^{x1a'}$, $SO_2R^{x1a'}$, $SO_2N(R^{x1a'})_2$, $C(O)R^{x1a'}$; $C(O)OR^{x1a'}$, $C(O)N(R^{x1a'})_2$, wherein $R^{x1a'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{x1b}$ is selected from $L^1$, $R^{x1b'}$, $OR^{x1b'}$, $N(R^{x1b'})_2$, $SO_2R^{x1b'}$, $SO_2N(R^{x1b'})_2$, $C(O)R^{x1b'}$; $C(O)OR^{x1b'}$, $OC(O)R^{x1b'}$; $C(O)N(R^{x1b'})_2$, $N(R^{x1b'})C(O)R^{x1b'}$, $OC(O)N(R^{x1b'})_2$, $N(R^{x1b'})C(O)N(R^{x1b'})_2$, wherein $R^{x1b'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{x1b1}$ is selected from $L^1$, $R^{x1b1'}$, $OR^{x1b1'}$, $N(R^{x1b1'})_2$, $SO_2R^{x1b1'}$, $SO_2N(R^{x1b1'})_2$, $C(O)R^{x1b1'}$; $C(O)OR^{x1b1'}$, $OC(O)R^{x1b1'}$; $C(O)N(R^{x1b1'})_2$, $N(R^{x1b1'})C(O)R^{x1b1'}$, $OC(O)N(R^{x1b1'})_2$, $N(R^{x1b1'})C(O)N(R^{x1b1'})_2$, wherein $R^{x1b1'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{x1b2}$ is selected from $L^1$, $R^{x1b2'}$, $OR^{x1b2'}$, $N(R^{x1b2'})_2$, $SO_2R^{x1b2'}$, $SO_2N(R^{x1b2'})_2$, $CO(O)R^{x1b2'}$; $C(O)OR^{x1b2'}$, $OC(O)R^{x1b2'}$; $C(O)N(R^{x1b2'})_2$, $N(R^{x1b2'})C(O)R^{x1b2'}$, $OC(O)N(R^{x1b2'})_2$, $N(R^{x1b2'})C(O)N(R^{x1b2'})_2$, wherein $R^{x1b2'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{x1c}$ is selected from $L^1$, $R^{x1c'}$, $OR^{x1c'}$, $N(R^{x1c'})_2$, $SO_2R^{x1c'}$, $SO_2N(R^{x1c'})_2$, $C(O)R^{x1c'}$; $C(O)OR^{x1c'}$, $OC(O)R^{x1c'}$; $C(O)N(R^{x1c'})_2$, $N(R^{x1c'})C(O)R^{x1c'}$, $OC(O)N(R^{x1c'})_2$, $N(R^{x1c'})C(O)N(R^{x1c'})_2$, wherein $R^{x1c'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{x1c1}$ is selected from $L^1$, $R^{x1c1'}$, $OR^{x1c1'}$, $N(R^{x1c1'})_2$, $SO_2R^{x1c1'}$, $SO_2N(R^{x1c1'})_2$, $C(O)R^{x1c1'}$; $C(O)OR^{x1c1'}$, $OC(O)R^{x1c1'}$; $C(O)N(R^{x1c1'})_2$, $N(R^{x1c1'})C(O)R^{x1c1'}$, $OC(O)N(R^{x1c1'})_2$, $N(R^{x1c1'})C(O)N(R^{x1c1'})_2$, wherein $R^{x1c1'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein $R^{x1c2}$ is selected from $L^1$, $R^{x1c2'}$, $OR^{x1c2'}$, $N(R^{x1c2'})_2$, $SO_2R^{x1c2'}$, $SO_2N(R^{x1c2'})_2$, $C(O)R^{x1c2'}$; $C(O)OR^{x1c2'}$, $OC(O)R^{x1c2'}$; $C(O)N(R^{x1c2'})_2$, $N(R^{x1c2'})C(O)R^{x1c2'}$, $OC(O)N(R^{x1c2'})_2$, $N(R^{x1c2'})C(O)N(R^{x1c2'})_2$, wherein $R^{x1c2'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
wherein any two or more of $R^{x1}$, $R^n$, $R^{1a}$, $R^{1b}$, $R^{1c}$, $R^{1d}$, $R^{x1a}$, $R^{x1b}$, $R^{x1b1}$, $R^{x1b2}$, $R^{x1c}$, $R^{x1c1}$, and $R^{x1c2}$ may together form a ring;
wherein $Ar^1$ contains a single $L^1$ group.

In some embodiments, X is S, while in others X is O.
Exemplary $Ar^1$ heterocycles include structures having the formula:

A-1

In certain embodiments, one of $R^{1a}$, $R^{1b}$, $R^{1c}$, and $R^{1d}$ is $L^1$, and the other three groups are hydrogen. For instance, $R^{1a}$ can be $L^1$, and $R^{1b}$, $R^{1c}$, and $R^{1d}$ are hydrogen; or $R^{1b}$ can be $L^1$, and $R^{1a}$, $R^{1c}$, and $R^{1d}$ are hydrogen; or $R^{1c}$ can be $L^1$, and $R^{1a}$, $R^{1b}$, and $R^{1d}$ are hydrogen; or $R^{1d}$ can be $L^1$, and $R^{1a}$, $R^{1b}$, and $R^{1c}$ are hydrogen.

In certain embodiments $X^{1a}$ is NH, $X^{1b}$ is N, and $X^{2c}$ is CH.

In some cases, $Ar^2$ can be an aryl or heterocycle having the formula:

wherein $X^{2a}$ is selected from —N=CR$^{x2a1}$-; —CR$^{x2a1}$=N—; O, S, and NR$^{x2a}$;

$X^{1b}$ is selected from N, CR$^{x2b}$, —N=CR$^{x2b1}$-; and —CR$^{x2b1}$=CR$^{x1b2}$-;

$X^{1c}$ is selected from N, CR$^{x2c}$, —CR$^{x2c1}$=CR$^{x2c2}$-;

wherein $R^{2a}$ is selected from $L^2$, $R^{2a'}$, OR$^{2a'}$, N(R$^{2a'}$)$_2$, SO$_2$R$^{2a'}$, SO$_2$N(R$^{2a'}$)$_2$, C(O)R$^{2a'}$; C(O)OR$^{2a'}$, OC(O)R$^{2a'}$; C(O)N(R$^{2a'}$)$_2$, N(R$^{2a'}$)C(O)R$^{2a'}$, OC(O)N(R$^{2a'}$)$_2$, N(R$^{2a'}$)C(O)N(R$^{2a'}$)$_2$, wherein $R^{2a'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{2b}$ is selected from $L^2$, $R^{2b'}$, OR$^{2b'}$, N(R$^{2b'}$)$_2$, SO$_2$R$^{2b'}$, SO$_2$N(R$^{2b'}$)$_2$, C(O)R$^{2b'}$; C(O)OR$^{2b'}$, OC(O)R$^{2b'}$; C(O)N(R$^{2b'}$)$_2$, N(R$^{2b'}$)C(O)R$^{2b'}$, OC(O)N(R$^{2b'}$)$_2$, N(R$^{2b'}$)C(O)N(R$^{2b'}$)$_2$, wherein $R^{2b'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{2c}$ is selected from $L^2$, $R^{2c'}$, OR$^{2c'}$, N(R$^{2c'}$)$_2$, SO$_2$R$^{2c'}$, SO$_2$N(R$^{2c'}$)$_2$, C(O)R$^{2c'}$; C(O)OR$^{2c'}$, OC(O)R$^{2c'}$; C(O)N(R$^{2c'}$)$_2$, N(R$^{2c'}$)C(O)R$^{2c'}$, OC(O)N(R$^{2c'}$)$_2$, N(R$^{2c'}$)C(O)N(R$^{2c'}$)$_2$, wherein $R^{2c'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{2d}$ is selected from $L^2$, $R^{2d'}$, OR$^{2d'}$, N(R$^{2d'}$)$_2$, SO$_2$R$^{2d'}$, SO$_2$N(R$^{2d'}$)$_2$, C(O)R$^{2d'}$; C(O)OR$^{2d'}$, OC(O)R$^{2d'}$; C(O)N(R$^{2d'}$)$_2$, N(R$^{2d'}$)C(O)R$^{2d'}$, OC(O)N(R$^{2d'}$)$_2$, N(R$^{2d'}$)C(O)N(R$^{2d'}$)$_2$, wherein $R^{2d'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{x2a1}$ is selected from $L^2$, $R^{x2a1'}$, SO$_2$R$^{x2a1'}$, SO$_2$N(R$^{x2a1'}$)$_2$, C(O)R$^{x2a1'}$; C(O)OR$^{x2a1'}$, C(O)N(R$^{x2a1'}$)$_2$, wherein $R^{x2a1'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{x2b}$ is selected from $L^2$, $R^{x2b'}$, OR$^{x2b'}$, N(R$^{x2b'}$)$_2$, SO$_2$R$^{x2b'}$, SO$_2$N(R$^{x2b'}$)$_2$, C(O)R$^{x2b'}$; C(O)OR$^{x2b'}$, OC(O)R$^{x2b'}$; C(O)N(R$^{x2b'}$)$_2$, N(R$^{x2b'}$)C(O)R$^{x2b'}$, OC(O)N(R$^{x2b'}$)$_2$, N(R$^{x2b'}$)C(O)N(R$^{x2b'}$)$_2$, wherein $R^{x2b'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{x2b1}$ is selected from $L^2$, $R^{x2b1'}$, OR$^{x2b1'}$, N(R$^{x2b1'}$)$_2$, SO$_2$R$^{x2b1'}$, SO$_2$N(R$^{x2b1'}$)$_2$, C(O)R$^{x2b1'}$; C(O)OR$^{x2b1'}$, OC(O)R$^{x2b1'}$; C(O)N(R$^{x2b1'}$)$_2$, N(R$^{x2b1'}$)C(O)R$^{x2b1'}$, OC(O)N(R$^{x2b1'}$)$_2$, N(R$^{x2b1'}$)C(O)N(R$^{x2b1'}$)$_2$, wherein $R^{x2b1'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{x2b2}$ is selected from $L^2$, $R^{x2b2'}$, OR$^{x2b2'}$, N(R$^{x2b2'}$)$_2$, SO$_2$R$^{x2b2'}$, SO$_2$N(R$^{x2b2'}$)$_2$, C(O)R$^{x2b2'}$; C(O)OR$^{x2b2'}$, OC(O)R$^{x2b2'}$; C(O)N(R$^{x2b2'}$)$_2$, N(R$^{x2b2'}$)C(O)R$^{x2b2'}$, OC(O)N(R$^{x2b2'}$)$_2$, N(R$^{x2b2'}$)C(O)N(R$^{x2b2'}$)$_2$, wherein $R^{x2b2'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{x2c}$ is selected from $L^2$, $R^{x2c'}$, OR$^{x2c'}$, N(R$^{x2c'}$)$_2$, SO$_2$R$^{x2c'}$, SO$_2$N(R$^{x2c'}$)$_2$, C(O)R$^{x2c'}$; C(O)OR$^{x2c'}$, OC(O)R$^{x2c'}$; C(O)N(R$^{x2c'}$)$_2$, N(R$^{x2c'}$)C(O)R$^{x2c'}$, OC(O)N(R$^{x2c'}$)$_2$, N(R$^{x2c'}$)C(O)N(R$^{x2c'}$)$_2$, wherein $R^{x2c'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{x2c1}$ is selected from $L^2$, $R^{x2c1'}$, OR$^{x2c1'}$, N(R$^{x2c1'}$)$_2$, SO$_2$R$^{x2c1'}$, SO$_2$N(R$^{x2c1'}$)$_2$, C(O)R$^{x2c1'}$; C(O)OR$^{x2c1'}$, OC(O)R$^{x2c1'}$; C(O)N(R$^{x2c1'}$)$_2$, N(R$^{x2c1'}$)C(O)R$^{x2c1'}$, OC(O)N(R$^{x2c1'}$)$_2$, N(R$^{x2c1'}$)C(O)N(R$^{x2c1'}$)$_2$, wherein $R^{x2c1'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein $R^{x2c2}$ is selected from $L^2$, $R^{x2c2'}$, OR$^{x2c2'}$, N(R$^{x2c2'}$)$_2$, SO$_2$R$^{x2c2'}$, SO$_2$N(R$^{x2c2'}$)$_2$, C(O)R$^{x2c2'}$; C(O)OR$^{x2c2'}$, OC(O)R$^{x2c2'}$; C(O)N(R$^{x2c2'}$)$_2$, N(R$^{x2c2'}$)C(O)R$^{x2c2'}$, OC(O)N(R$^{x2c2'}$)$_2$, N(R$^{x2c2'}$)C(O)N(R$^{x2c2'}$)$_2$, wherein $R^{x2c2'}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein any two or more of $R^{x2}$, $R^N$, $R^{2a}$, $R^{2b}$, $R^{2c}$, $R^{2d}$, $R^{x2a}$, $R^{x2b}$, $R^{x2b1}$, $R^{x2b2}$, $R^{x2c}$, $R^{x2c1}$, and $R^{x2c2}$ may together form a ring;

wherein $Ar^2$ contains a single $L^2$ group.

In certain embodiments, $Ar^2$ can be a group of:

A-2

B-2

C-2

D-2

-continued

E-2

F-2

G-2

H-2

I-2

J-2

K-2

L-2

M-2

N-2

In certain embodiments, one of $R^{2a}$, $R^{2b}$, $R^{2c}$, $R^{2d}$ is $L^2$, and the other three groups are hydrogen. For instance, $R^{2a}$ can be $L^2$, and $R^{2b}$, $R^{2c}$, and $R^{2d}$ are hydrogen; or $R^{2b}$ can be $L^2$, and $R^{2a}$, $R^{2c}$, and $R^{2d}$ are hydrogen; or $R^{2c}$ can be $L^2$, and $R^{2a}$, $R^{2b}$, and $R^{2d}$ are hydrogen; or $R^{2d}$ can be $L^2$, and $R^{2a}$, $R^{2b}$, and $R^{2c}$ are hydrogen.

In certain embodiments $X^{2a}$ is NH, $X^{2b}$ is N, and $X^{2c}$ is CH.

In some embodiments, $R^{1c}$ is $L^1$ and $R^{2c}$ is $L^2$, or $R^{1b}$ is $L^1$ and $R^{2c}$ is $L^2$, or $R^{1b}$ is $L^1$ and $R^{2b}$ is $L^2$, i.e., when $Ar^1$=B-1 and $Ar^2$=B2, compounds having the formula:

or a pharmaceutically acceptable salt thereof.

wherein $R^{x1}$, $R^n$, $R^{1a}$, $R^{1b}$, $R^{1c}$, $R^{1d}$, $R^{x1a}$, $R^{x1b}$, $R^{x1b1}$, $R^{x1b2}$, $R^{x1c}$, $R^{x1c1}$, $R^{x1c2}$, $R^{x2}$, $R^N$, $R^{2a}$, $R^{2b}$, $R^{2c}$, $R^{2d}$, $R^{x2a}$, $R^{x2b}$, $R^{x2b1}$, $R^{x2b2}$, $R^{x2c}$, $R^{x2c1}$, and $R^{x2c2}$ are as defined above.

Other embodiments include compounds wherein:

$R^{1a}$ is $L^1$ and $R^{2a}$ is $L^2$; or
$R^{1a}$ is $L^1$ and $R^{2b}$ is $L^2$; or
$R^{1a}$ is $L^1$ and $R^{2c}$ is $L^2$; or
$R^{1a}$ is $L^1$ and $R^{2d}$ is $L^2$; or
$R^{1b}$ is $L^1$ and $R^{2a}$ is $L^2$; or
$R^{1b}$ is $L^1$ and $R^{2b}$ is $L^2$; or
$R^{1b}$ is $L^1$ and $R^{2c}$ is $L^2$; or
$R^{1b}$ is $L^1$ and $R^{2d}$ is $L^2$; or
$R^{1c}$ is $L^1$ and $R^{2a}$ is $L^2$; or
$R^{1c}$ is $L^1$ and $R^{2b}$ is $L^2$; or
$R^{1c}$ is $L^1$ and $R^{2c}$ is $L^2$; or
$R^{1c}$ is $L^1$ and $R^{2d}$ is $L^2$; or
$R^{1d}$ is $L^1$ and $R^{2a}$ is $L^2$; or
$R^{1d}$ is $L^1$ and $R^{2b}$ is $L^2$; or
$R^{1d}$ is $L^1$ and $R^{2c}$ is $L^2$; or
$R^{1d}$ is $L^1$ and $R^{2d}$ is $L^2$.

These linkage patterns are equally applicable to heterocycles A-1-N-1, and A-2-N-2. For instance:

when $Ar^1$ is A-1 and $Ar^2$ is A-2; $Ar^1$ is B-1 and $Ar^2$ is A-2; $Ar^1$ is C-1 and $Ar^2$ is A-2; $Ar^1$ is D-1 and $Ar^2$ is A-2; $Ar^1$ is E-1 and $Ar^2$ is A-2; $Ar^1$ is F-1 and $Ar^2$ is A-2; $Ar^1$ is G-1 and $Ar^2$ is A-2; $Ar^1$ is H-1 and $Ar^2$ is A-2; $Ar^1$ is I-1 and $Ar^2$ is A-2; $Ar^1$ is J-1 and $Ar^2$ is A-2; $Ar^1$ is K-1, and $Ar^2$ is A-2; $Ar^1$ is L-1 and $Ar^2$ is A-2; $Ar^1$ is M-1 and $Ar^2$ is A-2; $Ar^1$ is N-1 and $Ar^2$ is A-2;

when $Ar^1$ is A-1 and $Ar^2$ is B-2; $Ar^1$ is B-1 and $Ar^2$ is B-2; $Ar^1$ is C-1 and $Ar^2$ is B-2; $Ar^1$ is D-1 and $Ar^2$ is B-2; $Ar^1$ is E-1 and $Ar^2$ is B-2; $Ar^1$ is F-1 and $Ar^2$ is B-2; $Ar^1$ is G-1 and $Ar^2$ is B-2; $Ar^1$ is H-1 and $Ar^2$ is B-2; $Ar^1$ is I-1 and $Ar^2$ is B-2; $Ar^1$ is J-1 and $Ar^2$ is B-2; $Ar^1$ is K-1, and $Ar^2$ is B-2; $Ar^1$ is L-1 and $Ar^2$ is B-2; $Ar^1$ is M-1 and $Ar^2$ is B-2; $Ar^1$ is N-1 and $Ar^2$ is B-2; when $Ar^1$ is A-1 and $Ar^2$ is C-2; $Ar^1$ is B-1 and $Ar^2$ is C-2; $Ar^1$ is C-1 and $Ar^2$ is C-2; $Ar^1$ is D-1 and $Ar^2$ is C-2; $Ar^1$ is E-1 and $Ar^2$ is C-2; $Ar^1$ is F-1 and $Ar^2$ is C-2; $Ar^1$ is G-1 and $Ar^2$ is C-2; $Ar^1$ is H-1 and $Ar^2$ is C-2; $Ar^1$ is I-1 and $Ar^2$ is C-2; $Ar^1$ is J-1 and $Ar^2$ is C-2; $Ar^1$ is K-1, and $Ar^2$ is C-2; $Ar^1$ is L-1 and $Ar^2$ is C-2; $Ar^1$ is M-1 and $Ar^2$ is C-2; $Ar^1$ is N-1 and $Ar^2$ is C-2;

when $Ar^1$ is A-1 and $Ar^2$ is D-2; $Ar^1$ is B-1 and $Ar^2$ is D-2; $Ar^1$ is C-1 and $Ar^2$ is D-2; $Ar^1$ is D-1 and $Ar^2$ is D-2; $Ar^1$ is E-1 and $Ar^2$ is D-2; $Ar^1$ is F-1 and $Ar^2$ is D-2; $Ar^1$ is G-1 and $Ar^2$ is D-2; $Ar^1$ is H-1 and $Ar^2$ is D-2; $Ar^1$ is I-1 and $Ar^2$ is D-2; $Ar^1$ is J-1 and $Ar^2$ is D-2; $Ar^1$ is K-1, and $Ar^2$ is D-2; $Ar^1$ is L-1 and $Ar^2$ is D-2; $Ar^1$ is M-1 and $Ar^2$ is D-2; $Ar^1$ is N-1 and $Ar^2$ is D-2;

when $Ar^1$ is A-1 and $Ar^2$ is E-2; $Ar^1$ is B-1 and $Ar^2$ is E-2; $Ar^1$ is C-1 and $Ar^2$ is E-2; $Ar^1$ is D-1 and $Ar^2$ is E-2; $Ar^1$ is E-1 and $Ar^2$ is E-2; $Ar^1$ is F-1 and $Ar^2$ is E-2; $Ar^1$ is G-1 and $Ar^2$ is E-2; $Ar^1$ is H-1 and $Ar^2$ is E-2; $Ar^1$ is I-1 and $Ar^2$ is E-2; $Ar^1$ is J-1 and $Ar^2$ is E-2; $Ar^1$ is K-1, and $Ar^2$ is E-2; $Ar^1$ is L-1 and $Ar^2$ is E-2; $Ar^1$ is M-1 and $Ar^2$ is E-2; $Ar^1$ is N-1 and $Ar^2$ is E-2;

when $Ar^1$ is A-1 and $Ar^2$ is F-2; $Ar^1$ is B-1 and $Ar^2$ is F-2; $Ar^1$ is C-1 and $Ar^2$ is F-2; $Ar^1$ is D-1 and $Ar^2$ is F-2; $Ar^1$ is E-1 and $Ar^2$ is F-2; $Ar^1$ is F-1 and $Ar^2$ is F-2; $Ar^1$ is G-1 and $Ar^2$ is F-2; $Ar^1$ is H-1 and $Ar^2$ is F-2; $Ar^1$ is I-1 and $Ar^2$ is F-2; $Ar^1$ is J-1 and $Ar^2$ is F-2; $Ar^1$ is K-1, and $Ar^2$ is F-2; $Ar^1$ is L-1 and $Ar^2$ is F-2; $Ar^1$ is M-1 and $Ar^2$ is F-2; $Ar^1$ is N-1 and $Ar^2$ is F-2;

when $Ar^1$ is A-1 and $Ar^2$ is G-2; $Ar^1$ is B-1 and $Ar^2$ is G-2; $Ar^1$ is C-1 and $Ar^2$ is G-2; $Ar^1$ is D-1 and $Ar^2$ is G-2; $Ar^1$ is E-1 and $Ar^2$ is G-2; $Ar^1$ is F-1 and $Ar^2$ is G-2; $Ar^1$ is G-1 and $Ar^2$ is G-2; $Ar^1$ is H-1 and $Ar^2$ is G-2; $Ar^1$ is I-1 and $Ar^2$ is G-2; $Ar^1$ is J-1 and $Ar^2$ is G-2; $Ar^1$ is K-1, and $Ar^2$ is G-2; $Ar^1$ is L-1 and $Ar^2$ is G-2; $Ar^1$ is M-1 and $Ar^2$ is G-2; $Ar^1$ is N-1 and $Ar^2$ is G-2;

when $Ar^1$ is A-1 and $Ar^2$ is H-2; $Ar^1$ is B-1 and $Ar^2$ is H-2; $Ar^1$ is C-1 and $Ar^2$ is H-2; $Ar^1$ is D-1 and $Ar^2$ is H-2; $Ar^1$ is E-1 and $Ar^2$ is H-2; $Ar^1$ is F-1 and $Ar^2$ is H-2; $Ar^1$ is G-1 and $Ar^2$ is H-2; $Ar^1$ is H-1 and $Ar^2$ is H-2; $Ar^1$ is I-1 and $Ar^2$ is H-2; $Ar^1$ is J-1 and $Ar^2$ is H-2; $Ar^1$ is K-1, and $Ar^2$ is H-2; $Ar^1$ is L-1 and $Ar^2$ is H-2; $Ar^1$ is M-1 and $Ar^2$ is H-2; $Ar^1$ is N-1 and $Ar^2$ is H-2;

when $Ar^1$ is A-1 and $Ar^2$ is I-2; $Ar^1$ is B-1 and $Ar^2$ is I-2; $Ar^1$ is C-1 and $Ar^2$ is I-2; $Ar^1$ is D-1 and $Ar^2$ is I-2; $Ar^1$ is E-1 and $Ar^2$ is I-2; $Ar^1$ is F-1 and $Ar^2$ is I-2; $Ar^1$ is G-1 and $Ar^2$ is I-2; $Ar^1$ is H-1 and $Ar^2$ is I-2; $Ar^1$ is I-1 and $Ar^2$ is I-2; $Ar^1$ is J-1 and $Ar^2$ is I-2; $Ar^1$ is K-1, and $Ar^2$ is I-2; $Ar^1$ is L-1 and $Ar^2$ is I-2; $Ar^1$ is M-1 and $Ar^2$ is I-2; $Ar^1$ is N-1 and $Ar^2$ is I-2;

when $Ar^1$ is A-1 and $Ar^2$ is J-2; $Ar^1$ is B-1 and $Ar^2$ is J-2; $Ar^1$ is C-1 and $Ar^2$ is J-2; $Ar^1$ is D-1 and $Ar^2$ is J-2; $Ar^1$ is E-1 and $Ar^2$ is J-2; $Ar^1$ is F-1 and $Ar^2$ is J-2; $Ar^1$ is G-1 and $Ar^2$ is J-2; $Ar^1$ is H-1 and $Ar^2$ is J-2; $Ar^1$ is I-1 and $Ar^2$ is J-2; $Ar^1$ is J-1 and $Ar^2$ is J-2; $Ar^1$ is K-1, and $Ar^2$ is J-2; $Ar^1$ is L-1 and $Ar^2$ is J-2; $Ar^1$ is M-1 and $Ar^2$ is J-2; $Ar^1$ is N-1 and $Ar^2$ is J-2;

when $Ar^1$ is A-1 and $Ar^2$ is K-2; $Ar^1$ is B-1 and $Ar^2$ is K-2; $Ar^1$ is C-1 and $Ar^2$ is K-2; $Ar^1$ is D-1 and $Ar^2$ is K-2; $Ar^1$ is E-1 and $Ar^2$ is K-2; $Ar^1$ is F-1 and $Ar^2$ is K-2; $Ar^1$ is G-1 and $Ar^2$ is K-2; $Ar^1$ is H-1 and $Ar^2$ is K-2; $Ar^1$ is I-1 and $Ar^2$ is K-2; $Ar^1$ is J-1 and $Ar^2$ is K-2; $Ar^1$ is K-1, and $Ar^2$ is K-2; $Ar^1$ is L-1 and $Ar^2$ is K-2; $Ar^1$ is M-1 and $Ar^2$ is K-2; $Ar^1$ is N-1 and $Ar^2$ is K-2;

when $Ar^1$ is A-1 and $Ar^2$ is L-2; $Ar^1$ is B-1 and $Ar^2$ is L-2; $Ar^1$ is C-1 and $Ar^2$ is L-2; $Ar^1$ is D-1 and $Ar^2$ is L-2; $Ar^1$ is E-1 and $Ar^2$ is L-2; $Ar^1$ is F-1 and $Ar^2$ is L-2; $Ar^1$ is G-1 and $Ar^2$ is L-2; $Ar^1$ is H-1 and $Ar^2$ is L-2; $Ar^1$ is I-1 and $Ar^2$ is L-2; $Ar^1$ is J-1 and $Ar^2$ is L-2; $Ar^1$ is K-1, and $Ar^2$ is L-2; $Ar^1$ is L-1 and $Ar^2$ is L-2; $Ar^1$ is M-1 and $Ar^2$ is L-2; $Ar^1$ is N-1 and $Ar^2$ is L-2;

when $Ar^1$ is A-1 and $Ar^2$ is M-2; $Ar^1$ is B-1 and $Ar^2$ is M-2; $Ar^1$ is C-1 and $Ar^2$ is M-2; $Ar^1$ is D-1 and $Ar^2$ is M-2; $Ar^1$ is E-1 and $Ar^2$ is M-2; $Ar^1$ is F-1 and $Ar^2$ is M-2; $Ar^1$ is G-1 and $Ar^2$ is M-2; $Ar^1$ is H-1 and $Ar^2$ is M-2; $Ar^1$ is I-1 and $Ar^2$ is M-2; $Ar^1$ is J-1 and $Ar^2$ is M-2; $Ar^1$ is K-1, and $Ar^2$ is M-2; $Ar^1$ is L-1 and $Ar^2$ is M-2; $Ar^1$ is M-1 and $Ar^2$ is M-2; $Ar^1$ is N-1 and $Ar^2$ is M-2; or when $Ar^1$ is A-1 and $Ar^2$ is N-2; $Ar^1$ is B-1 and $Ar^2$ is N-2; $Ar^1$ is C-1 and $Ar^2$ is N-2; $Ar^1$ is D-1 and $Ar^2$ is N-2; $Ar^1$ is E-1 and $Ar^2$ is N-2; $Ar^1$ is F-1 and $Ar^2$ is N-2; $Ar^1$ is G-1 and $Ar^2$ is N-2; $Ar^1$ is H-1 and $Ar^2$ is N-2; $Ar^1$ is I-1 and $Ar^2$ is N-2; $Ar^1$ is J-1 and $Ar^2$ is N-2; $Ar^1$ is K-1, and $Ar^2$ is N-2; $Ar^1$ is L-1 and $Ar^2$ is N-2; $Ar^1$ is M-1 and $Ar^2$ is N-2; $Ar^1$ is N-1 and $Ar^2$ is N-2;

In particular embodiments of the above compounds, $L^1$ and $L^2$ are each null; for instance, when $Ar^1$=B-1 and $Ar^2$=B-2, $R^{1b}$ is $L^1$ and $R^{2c}$ is $L^2$, such a compound would have the formula:

The skilled person understands the structures of compounds formed by other embodiments defining alternative selections for $Ar^1$, $Ar^2$, $L^1$ and $L^2$ as defined above. In certain cases, it is preferred that:

$R^{1a}$ can be selected from H, $C_{1-8}$alkyl, F, Cl, Br, I, $NO_2$, CN, $OR^{1a'}$, wherein $R^{1a'}$ is hydrogen or $C_{1-8}$alkyl;

$R^{1b}$ can be selected from H, $C_{1-8}$alkyl, F, Cl, Br, I, $NO_2$, CN, $OR^{1b'}$, wherein $R^{1b'}$ is hydrogen or $C_{1-8}$alkyl;

$R^{1c}$ can be selected from H, $C_{1-8}$alkyl, F, Cl, Br, I, $NO_2$, CN, $OR^{1c'}$, wherein $R^{1c'}$ is hydrogen or $C_{1-8}$alkyl;

$R^{1d}$ can be selected from H, $C_{1-8}$alkyl, F, Cl, Br, I, $NO_2$, CN, $OR^{1c'}$, wherein $R^{1c'}$ is hydrogen or $C_{1-8}$alkyl;

$R^{x1}$ can be selected from H, $C_{1-8}$alkyl;

$R^{x1a}$ can be selected from H, $C_{1-8}$alkyl;

$R^{x1c}$ can be selected from H, $C_{1-8}$alkyl;

$R^{x1b}$ can be selected from H, $C_{1-8}$alkyl;

$R^{x1b1}$ can be selected from H, $C_{1-8}$alkyl, F, Cl, Br, I, $NO_2$, CN, OH or $OC_{1-8}$alkyl;

$R^{x1c1}$ can be selected from H, $C_{1-8}$alkyl, F, Cl, Br, I, $NO_2$, CN, OH or $OC_{1-8}$alkyl;

$R^{x1c2}$ can be selected from H, $C_{1-8}$alkyl, F, Cl, Br, I, $NO_2$, CN, OH or $OC_{1-8}$alkyl;

$R^{2a}$ can be selected from H, $C_{1-8}$alkyl, F, Cl, Br, I, $NO_2$, CN, $OR^{2a'}$, wherein $R^{2a'}$ is hydrogen or $C_{1-8}$alkyl;

$R^{2b}$ can be selected from H, $C_{1-8}$alkyl, F, Cl, Br, I, $NO_2$, CN, $OR^{2b'}$, wherein $R^{2b'}$ is hydrogen or $C_{1-8}$alkyl;

$R^{2c}$ can be selected from H, $C_{1-8}$alkyl, F, Cl, Br, I, $NO_2$, CN, $OR^{2c'}$, wherein $R^{2c'}$ is hydrogen or $C_{1-8}$alkyl;

$R^{2d}$ can be selected from H, $C_{1-8}$alkyl, F, Cl, Br, I, $NO_2$, CN, $OR^{2c'}$, wherein $R^{2c'}$ is hydrogen or $C_{1-8}$alkyl;

$R^{x2}$ can be selected from H, $C_{1-8}$alkyl;

$R^{x2a}$ can be selected from H, $C_{1-8}$alkyl;

$R^{x2c}$ can be selected from H, $C_{1-8}$alkyl;

$R^{x2b}$ can be selected from H, $C_{1-8}$alkyl;

$R^{x2b1}$ can be selected from H, $C_{1-8}$alkyl, F, Cl, Br, I, $NO_2$, CN, OH or $OC_{1-8}$alkyl;

$R^{x2c1}$ can be selected from H, $C_{1-8}$alkyl, F, Cl, Br, I, $NO_2$, CN, OH or $OC_{1-8}$alkyl;

$R^{x2c2}$ can be selected from H, $C_{1-8}$alkyl, F, Cl, Br, I, $NO_2$, CN, OH or $OC_{1-8}$alkyl; wherein any two or more of R groups may together form a ring.

The compounds disclosed herein may be used to treat a variety of different organ injuries in adults, juveniles, infants, and/or neonates. For instance, in some embodiments, the injured organ is part of the central nervous system or cerebrovascular system. In other embodiments, the injured organ is the heart or kidney. The compounds disclosed herein may be used to treat injuries stemming from ischemic events. In some instances, the compounds disclosed herein may be used to treat injuries resulting from stroke, cardiac arrest, traumatic brain injury, hemorrhagic shock, or subarachnoid hemorrhage.

In certain embodiments, the compounds disclosed herein may be used to treat injuries in infants and/or neonates. For instance, the compounds may be used to treat perinatal asphyxia and/or viral neonatal encephalitis.

The compounds disclosed herein may be used to treat injuries diagnosed by one or more of the following tests: neuroimaging tests (e.g. CT, MRI, PET, DTI, Laser-Doppler), biomarker tests (e.g. blood or CSF GFAP or NSE levels), behavioral/cognitive tests (e.g. encephalopathy), and neurological scores (e.g. Glasgow outcome score, modified Rankin Scale, Cerebral Performance Category, and Mini-Mental State Examination).

The compounds disclosed herein may be provided in a wide variety of pharmaceutical compositions. Such compositions include, but are not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, modified release formulations, delayed release formulations, extended release formulations, pulsatile release formulations, dual release formulations and the like. Liquid or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention.

Suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

The compounds disclosed herein may be administered by a number of different routes. For instance, the compounds may be administered orally, transdermally, intravenously, subcutaneously, by inhalation, or by intracerebroventricular delivery.

EXAMPLES

The following examples are for the purpose of illustration of the invention only and are not intended to limit the scope of the present invention in any manner whatsoever.

Example 1: In Vitro Screen of NSC13378, NSC74429, and NSC25247 on the Staurosporine (STS) Injury Assay

NSC 13378

NSC 74429

NSC 25247

Primary rat cortical neurons were cultured on poly-D-lysine coated 96-well plates at a density of 1×105/well in Neurobasal medium+B27 supplement. 1/2 media swaps were given every 3 d. ARA-c was added to the medium on day in vitro (DIV) 3 to inhibit glial proliferation. On DIV9, maintenance media (2/3) was collected from plates and mixed with fresh media (1/3) to obtain ~67% conditioned medium (CM). Staurosporine (STS) and drugs were prepared in 100% DMSO and diluted in CM. Uninjured controls received an equal concentration of DMSO. Primary cortical neurons were incubated with +STS+drugs for in 100 µL/well CM. Cell viability was determined 24 h later (DIV10) by CELLTITER-BLUE® (n=10 replicates/group). (A) NSC13378 failed to protect whereas 25-50 µM NSC74429 was potently neuroprotective. (B) 50 µM NSC25247 was mildly neuroprotective. Data were analyzed by 1-Way-ANOVA and Newman-Keuls Multiple Comparison Test. Results are provided in FIG. 1. Graphs show Mean+SEM. Data are significant at p<0.05. Conclusion: NSC74429 is a potent a neuroprotectant as determined by the STS cell death assay.

Example 2: In Vitro Screen of NSC74429 and NSC25247 on Glutamate-Excitotoxicity and Hydrogen Peroxide ($H_2O_2$)-Oxidative Stress Assays Primary rat cortical neurons were cultured on poly-D-lysine coated 96-well plates at a density of 1×105/well in Neurobasal medium+B27 supplement. 1/2 media swaps were given every 3 d. ARA-c was added to the maintenance medium on day in vitro (DIV) 3 to inhibit glial proliferation. Results are presented in FIG. 2. (A) On DIV9, maintenance media (2/3) was collected from plates and mixed with fresh media (1/3) to obtain ~67% conditioned medium (CM). Cells were washed once with balanced salt solution (BSS supplemented with 5 mM glucose; 200 µL/well). BSS was replaced with BSS containing 10 µM glutamic acid, and incubated on cells 5 min to induce excitotoxicity. Glutamic acid/BSS was replaced with 100 µL/well CM, containing DMSO (control) or drugs, and returned to the incubator for 24 h (n=10 replicates/group). (B) DIV9 cells were washed once with BSS, injured 35 min with 40 µM $H_2O_2$ dissolved in BSS, and replaced with 100 µL/well CM containing DMSO (control) or drugs. Cell viability was determined 24 h later (DIV10) by addition of 20 µL/well CELLTITER-BLUE® (n=10 replicates/group). Data were analyzed by 1-Way-ANOVA and Newman-Keuls Multiple Comparison Test. Graphs show Mean+SEM. Data are significant at p<0.05. Excitotoxicity is a major cause of neuronal death across the spectrum of CNS injury. Importantly, Sierecki and colleagues reported that the $IC_{50}$ of NSC74429 to block PHLPP2 is 5 µM. We observed that 25 µM NSC74429 (5× higher than the $IC_{50}$ to block PHLPPs) was insufficient to decrease glutamate-induced neuronal death, whereas 50 µM NSC74429 reduced excitotoxic injury. Thus, our findings support the concept that the neuroprotective properties of NSC74429 do not involve the inhibition of PHLPPs, based on the effective concentration required to decrease excitotoxic cell death. Conclusion: NSC74429 decreases cell death induced by excitotoxity or oxidative stress in neurons.

Figure 1:
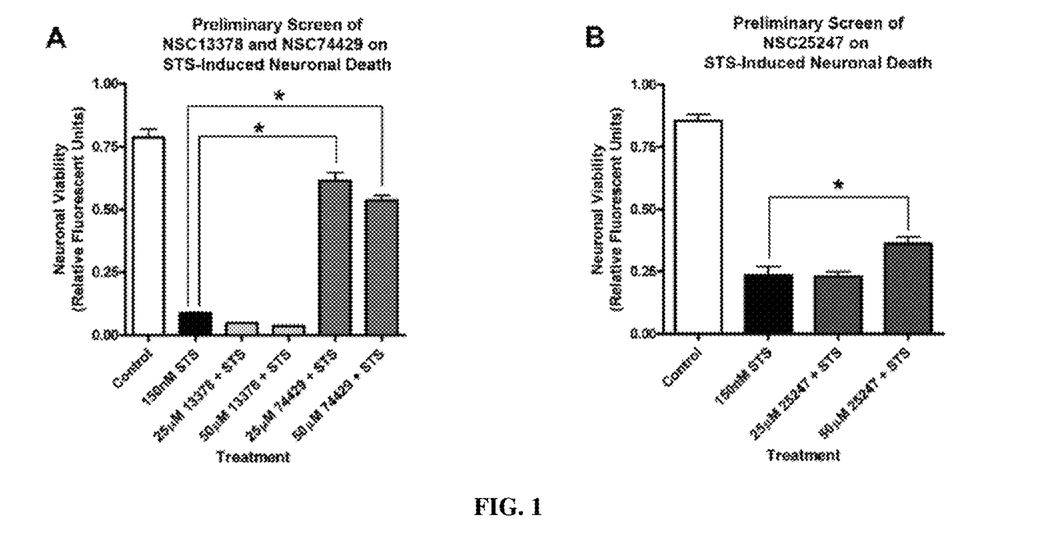
FIG. 1 depicts an in vitro screen of NSC13378, NSC74429, and NSC25247 on the staurosporine injury assay.
Figure 2:
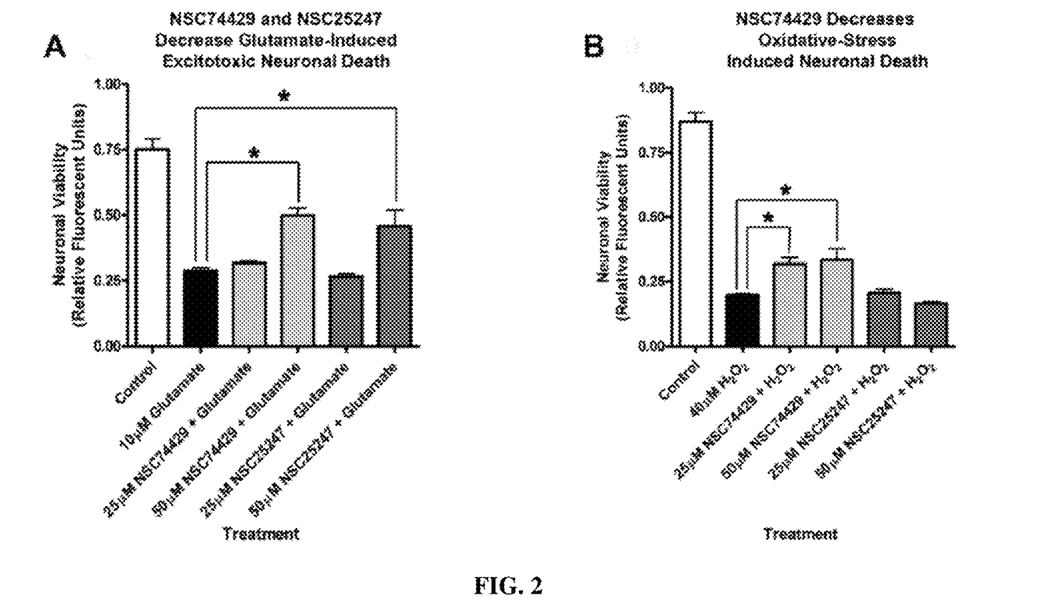
FIG. 2 depicts an in vitro screen of NSC74429 and NSC25247 on glutamate-excitotoxicity and hydrogen peroxide ($H_2O_2$)-oxidative stress assays.
Figure 3:
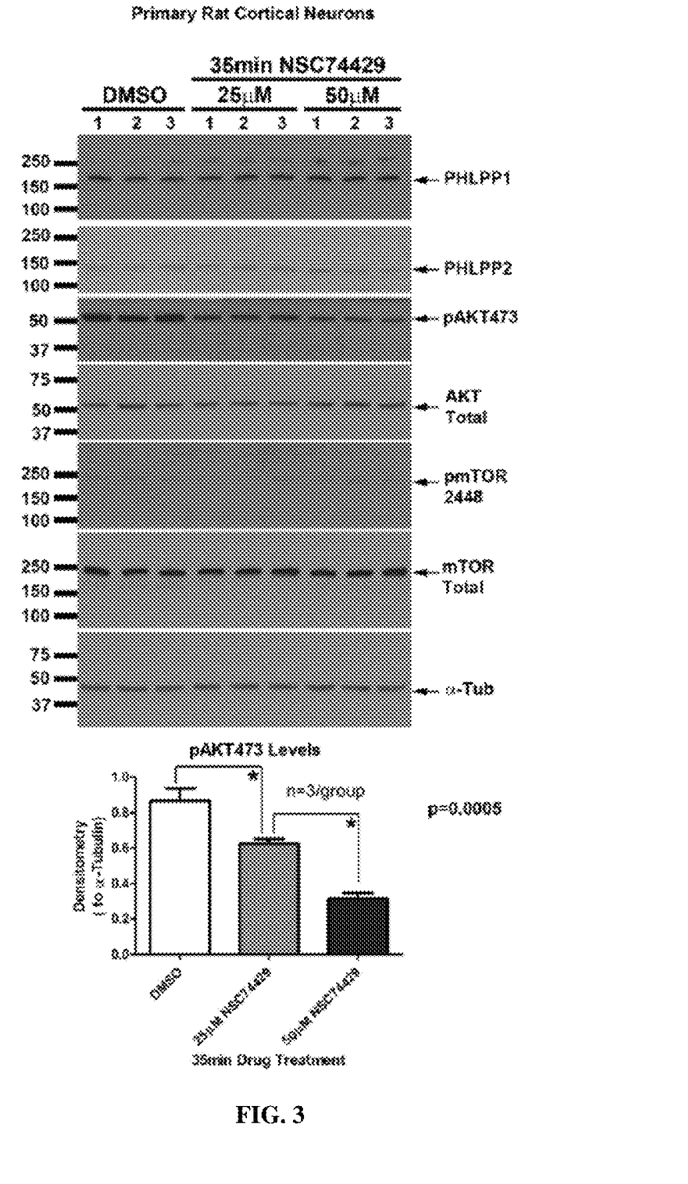
FIG. 3 depicts how NSC74429 unexpectedly inhibits pAKT473 levels in cultured primary rat cortical neurons.

Example 3: NSC74429 Unexpectedly Inhibits pAKT473 Levels in Cultured Primary Rat Cortical Neurons We reported that PHLPP inhibitors NSC117079 and NSC45586 dose-dependently increase pAKT473 levels in primary rat cortical neurons (Jackson et al., 2013). We tested if NSC74429 also increases pAKT473 levels using our published protocol. In brief, uninjured primary rat cortical neurons were maintained in Neurobasal+B27. Prior to treatments, neurons were given a supplement starvation period by exchanging maintenance media with basic Neurobasal (i.e. minus B27), and returned to a 37° C. incubator for 2 h. Neurons were subsequently treated 35 min with DMSO, 25 µM NSC74429, or 50 µM NSC74429 (diluted in basic Neurobasal). Western blots confirm that PHLPP1 and PHLPP2 isoforms are detected in rat cortical neurons. Results are presented in FIG. 3. Contrary to expectations, NSC74429 dose-dependently decreased pAKT473 levels but did not affect other phosphorylated proteins like mTOR (pmTOR2448). PHLPP inhibitors increase pAKT473 levels but NSC74429 had the opposite effect. Moreover, inhibition of pAKT473 is expected to promote cell death yet NSC74429 (AKT inhibitor) was neuroprotective as shown in FIG. 1 and FIG. 2. Our findings suggest that (1) NSC74429 is not a PHLPP inhibitor in living cells, and (2) the mechanism(s) of neuroprotection do not involve AKT activation and remain to be elucidated. Data were analyzed by 1-Way-ANOVA and Newman-Keuls Multiple Comparison Test. Graphs show Mean+SEM. Data are significant at p<0.05. Conclusion: Together PHLPP1 and PHLPP2 regulate the dephosphorylation of pAKT473 on AKT1, AKT2, and AKT3 isoforms. Our data show that the mechanism(s) of neuroprotection by NSC74429 do not involve PHLPP inhibition-mediated AKT activation.

Example 4: NSC74429 is a Potent Neuroprotectant in Adult Rat Asphyxia Cardiac Arrest (ACA)

Figure 4:
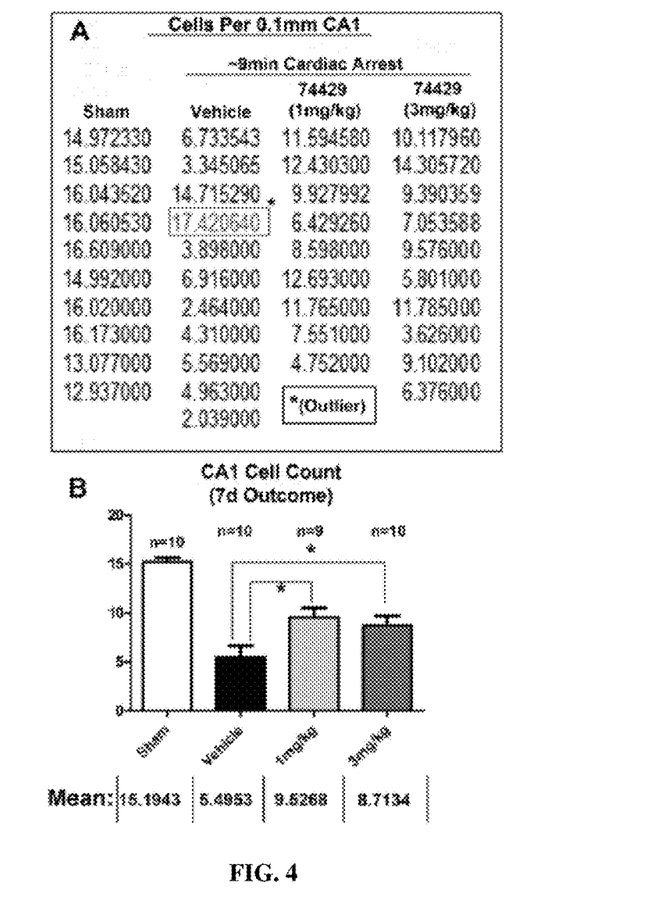
FIG. 4 depicts how NSC74429 is a potent neuroprotectant in adult rat asphyxia cardiac arrest (ACA).

We tested the therapeutic efficacy of NSC74429 in a model of brain injury (ACA) in which the blood brain barrier (BBB) remains intact. Male ~300 g Sprague Dawley rats were anesthetized on isoflurane (4% induction/2% maintenance on 50% $O_2$/50% $N_2$) and mechanically ventilated. The left femoral artery and vein were accessed and cannulated with heparinized-saline filled PE-50 tubing. EKG, mean arterial pressure (MAP), rectal temperature, and pectoralis temperature were continuously monitored. Body temperature was maintained to 37° C. Arterial blood gas measurements were analyzed and ventilator settings adjusted as needed to achieve normal $PaO_2$ and $PaCO_2$. 2 mg/kg cisatracurium was administered 5 min prior to CA to stop spontaneous breathing (i.e. neuromuscular blockage). The ventilator was disconnected. Mean arterial pressure (MAP) decreased over 2-3 min until reaching target no-flow (<10 mmHG). Following 5 min of no-flow CA, cardiopulmonary resuscitation was immediately initiated by injection with epinephrine and sodium bicarbonate. The ventilator was reconnected (100% $O_2$) and chest compressions administered (275 pbm). Rats which failed to achieve return of spontaneous circulation (ROSC) after 2 min of CPR were out of protocol and excluded from the study. 5 min after ROSC, rats were randomized to experimental therapy (1 mg/kg NSC74429, 3 mg/kg NSC74429) or vehicle control (24% DMSO in D5W). Results are presented in FIG. 4. (A) Values show hippocampal CA1 cell survival counts in sham vs. injured rats. (B) Statistical analysis of CA1 cell counts. Data were analyzed by 1-Way-ANOVA and Newman-Keuls Multiple Comparison Test. Graphs show Mean+SEM. Data are significant at p<0.05. Injured rats were randomized to treatment group, and drugs provided to a technician in de-identified coded vials. The technician that administered drug injections, and the technician that analyzed histology, were blinded to treatment group. A single value in the vehicle-injury group (indicated by a * in the table above) was a statistical outlier as determined by the Dixon's test and was removed from statistical analysis. Conclusion: NSC74429 is neuroprotective in an in vivo ischemia model. The integrity of the BBB is preserved in the ACA model which supports the concept that NSC74429 penetrates into the CNS.

Example 5: NSC74429 does not Increase pAKT473 Levels In Vivo

Figure 5:
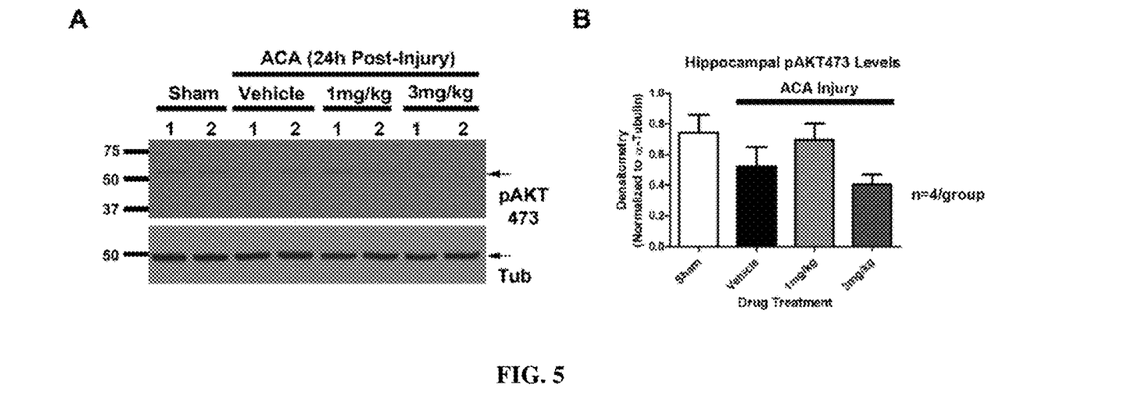
FIG. 5 depicts how NSC74429 does not increase pAKT473 levels in vivo.

A separate cohort of rats was used to generate hippocampal tissue homogenates. Rats were given ACA and subsequently treated with (a) vehicle, (b) 1 mg/kg NSC74429, or (c) 3 mg/kg NSC74429. Treatments were administered by iv bolus injection 5 min after ROSC, and a 2nd ip bolus injection 24 h post-injury. Shams were administered vehicle injections and preparatory surgery but were not injured. Rats were euthanized 1 h following the final drug injection and brain tissue collected for protein analysis. Results are presented in FIG. 5. NSC74429 did not increase pAKT473 levels in the injured hippocampus. These finding are consistent with in vitro observations, and suggest that hippocampal neuroprotection was independent of the PHLPP/AKT axis. Data were analyzed by 1-Way-ANOVA and Newman-Keuls Multiple Comparison Test. Injured rats were randomized to treatment group, and drugs provided to a technician in de-identified coded vials. The technician that administered drug injections was blinded to treatment group. Graphs show Mean+SEM. Data are significant at $p<0.05$. Conclusion: The mechanism(s) mediating NSC74429 induced hippocampal neuroprotection after ACA do not involve AKT activation and remain to be elucidated.

Example 6: NSC74429 is a Potent Neuroprotectant in an Adult Mouse Model of Controlled Cortical Impact Plus Hemorrhagic Shock (CCI+HS)

Figure 6:
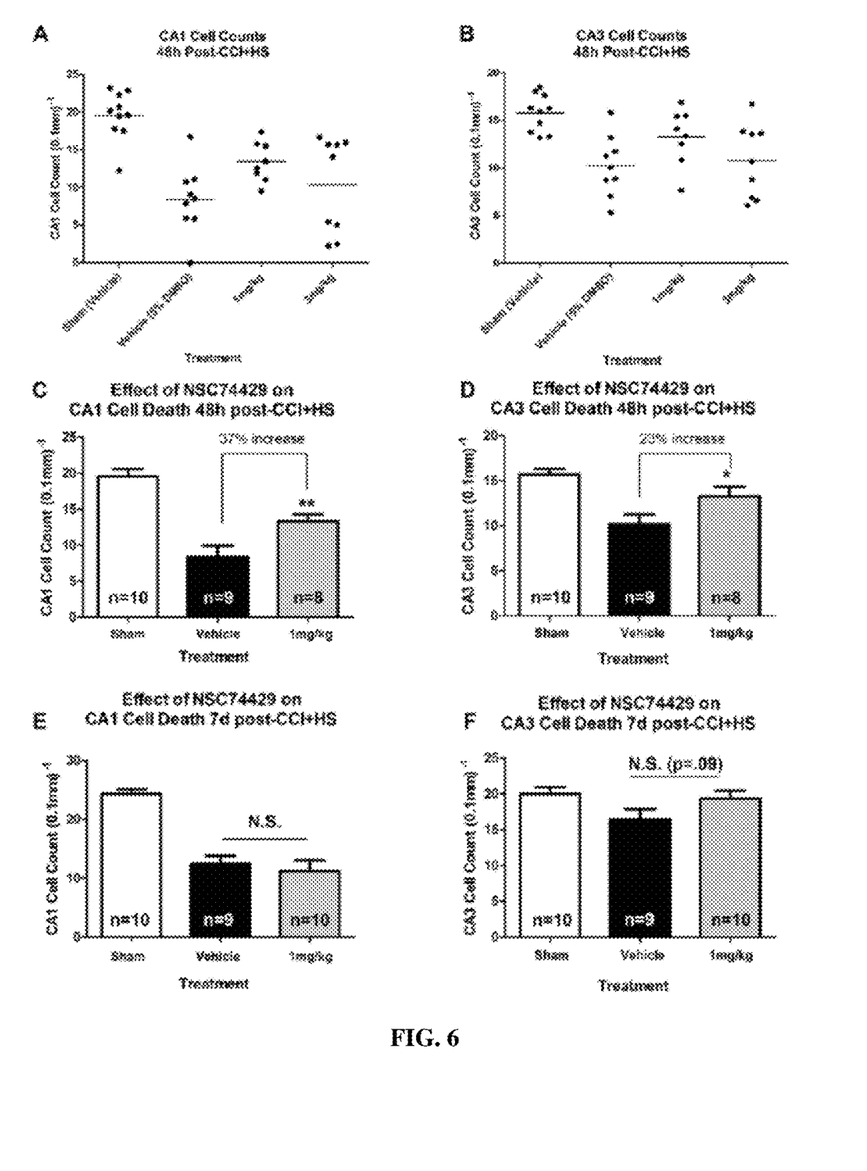
FIG. 6 depicts how NSC74429 is a potent neuroprotectant in an adult mouse model of controlled cortical impact plus hemorrhagic shock (CCI+HS).

Traumatic brain injury (TBI) compromises the BBB, making it easier for drugs to reach injured tissue, and TBI is also worsened by secondary injuries such as hypotension due to profound blood loss (HS). Adult male ~28 g C57BL/6 mice were anesthetized with isoflurane via a nose cone (4% induction/2% maintenance on 70% $N_2O$/30% $O_2$), given preparatory surgery, and sequentially injured by (1) a CCI-TBI and (2) HS, as reported by our group (Jackson et al., 2015). In brief, mice were given a moderate CCI above the left parietal cortex (impact tip velocity 5 m/s and cortical depth 1.0 mm). 5 min later, HS was initiated by withdrawing blood until mean arterial pressure (MAP) decreased from ~90 mmHG (normal) to ~25-27 mmHG (hypotensive). HS was maintained for 35 min. Mice were then volume resuscitated using lactated ringer's (LR) solution for 90 min to mimic pre-hospital care (targeted MAP of ~70 mmHG). Finally, shed blood was returned over 15 min to mimic definitive hospital care and MAP returned to normal. (A-D) In a first study we measured the acute neuroprotective effects of NSC74429 on hippocampal injury 48 h after CCI+HS. Mice were given an intravenous bolus injection of vehicle (5% DMSO in D5W) or NSC74429 (1 mg/kg or 3 mg/kg) immediately after the hospital phase (i.e. 110 mins after the initial CCI-injury). A second intraperitoneal injection was administered 24 h later, and brains collected for CA1/CA3 cell counts 48 h post-injury. One animal died in the vehicle-injury group and four animals died in the 3 mg/kg NSC74429 group prior to tissue collection. Results are presented in FIG. 6. (A and B) Scatter plots show CA1/CA3 cell counts in surviving animals. 1 mg/kg NSC74429 was neuroprotective. Hippocampal survival bifurcated in the 3 mg/kg high-dose group; some animals had improved CA1/CA3 survival vs. vehicle-injury whereas others were clearly made worse. Given that mortality was also higher with 3 mg/kg NSC74429 (4 vs. 1), we eliminated the high-dose group from further statistical analysis. (C and D) Statistical analysis of CA1/CA3 cell counts. 1 mg/kg NSC74429 significantly increased CA1 and CA3 cell survival 48 h post-injury. (E and F) A second study was done to test if NSC74429 neuroprotection is sustained chronically by 7 d post-injury. Only the low dose (1 mg/kg) was tested. Mice were injured as described above, given intravenous injection of vehicle or 1 mg/kg drug immediately following the hospital phase of HS, supplemental injections administered intraperitoneally at 24 h, 48 h, and 72 h post-injury, and brains collected for histology 7 d post-injury. CA1 survival was equivalent in both injured groups. In contrast, tissue sparing effects of NSC74429 were evident by 7 d post-injury in the CA3 region (~17.5% above vehicle injury) but did not reach statistical significance as our study was not powered to detect small effect sizes (e.g. 27 mice/group would be needed to detect a 20% increase in survival at 80% power, $\alpha=0.05$). Data were analyzed by 1-Way-ANOVA and Newman-Keuls Multiple Comparison Test. Graphs show Mean+SEM. Data are significant at $p<0.05$. Injured rats were randomized to treatment group, and drugs provided to a technician in de-identified coded vials. The technician that administered drug injections, and the technician that analyzed histology, were blinded to treatment group. Conclusion: NSC74429 is neuroprotective in the acute and chronic phase after injury in a severe trauma model.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method to reduce organ injury resulting from an ischemic event, comprising administering to a patient in need thereof a compound having the formula:

or a pharmaceutically acceptable salt thereof,
wherein
$L^1$ is null;
$R^{x1}$ is hydrogen;
X is S;
$R^{x2}$ is hydrogen;
$L^2$ is null;
$R^{1a}$ is selected from F, Cl, Br, $R^{1a'}$, $OR^{1a'}$, or $N(R^{1a'})_2$, wherein $R^{1a'}$ is in each case independently selected from hydrogen or $C_{1-8}$alkyl;
$R^{1b}$ is selected from $R^{1b'}$, $OR^{1b'}$, or $N(R^{1b'})_2$, wherein $R^{1b'}$ is in each case independently selected from hydrogen or $C_{1-8}$alkyl;
$R^{1c}$ is selected from $R^{1c'}$, $OR^{1c'}$, or $N(R^{1c'})_2$, wherein $R^{1c'}$ is in each case independently selected from hydrogen or $C_{1-8}$alkyl;
$R^{1d}$ is selected from $R^{1d'}$, $OR^{1d'}$, or $N(R^{1d'})_2$, wherein $R^{1d'}$ is in each case independently selected from hydrogen or $C_{1-8}$alkyl;
$R^{x1a}$ is selected from hydrogen or $C_{1-8}$alkyl;
$R^{x1c}$ is selected from $R^{x1c'}$, $OR^{x1c'}$, or $N(R^{x1c'})_2$, wherein $R^{x1c'}$ is in each case independently selected from hydrogen or $C_{1-8}$alkyl;
$R^{2a}$ is selected from $R^{2a'}$, $OR^{2a'}$, or $N(R^{2a'})_2$, wherein $R^{2a'}$ is in each case independently selected from hydrogen or $C_{1-8}$alkyl;
$R^{2b}$ is selected from $R^{2b'}$, $OR^{2b'}$, or $N(R^{2b'})_2$, wherein $R^{2b'}$ is in each case independently selected from hydrogen or $C_{1-8}$alkyl;
$R^{2c}$ is selected from $R^{2c'}$, $OR^{2c'}$, or $N(R^{2c'})_2$, wherein $R^{2c'}$ is in each case independently selected from hydrogen or $C_{1-8}$alkyl;
$R^{2d}$ is selected from $R^{2d'}$, $OR^{2d'}$, or $N(R^{2d'})_2$, wherein $R^{2d'}$ is in each case independently selected from hydrogen or $C_{1-8}$alkyl;
$R^{x2a}$ is selected from H and $C_{1-8}$alkyl;
$R^{x2c}$ is selected from $R^{x2c'}$, $OR^{x2c'}$, or $N(R^{x2c'})_2$, wherein $R^{x2c'}$ is in each case independently selected from hydrogen or $C_{1-8}$alkyl;
and wherein the injured organ is the brain, heart, or kidney.

2. The method of claim 1, wherein the compound has the formula:

3. The method of claim 1, wherein the compound has the formula:

4. The method of claim 1, wherein:
$R^{1a}$ is F, Cl, Br, I, H, $CH_3$, $CH_2CH_3$, $CH(CH_3)_2$, OH, $OCH_3$, $OCH_2OCH_3$, or $OCH(CH_3)_2$;
$R^{1b}$ is H, $CH_3$, $CH_2CH_3$, $CH(CH_3)_2$, OH, $OCH_3$, $OCH_2OCH_3$, or $OCH(CH_3)_2$;
$R^{1c}$ is H, $CH_3$, $CH_2CH_3$, $CH(CH_3)_2$, OH, $OCH_3$, $OCH_2OCH_3$, or $OCH(CH_3)_2$;
$R^{1d}$ is H, $CH_3$, $CH_2CH_3$, $CH(CH_3)_2$, OH, $OCH_3$, $OCH_2OCH_3$, or $OCH(CH_3)_2$;
$R^{x1c}$ is H, $CH_3$, $CH_2CH_3$, $CH(CH_3)_2$, OH, $OCH_3$, $OCH_2OCH_3$, or $OCH(CH_3)_2$;
$R^{x1a}$ is H, $CH_3$, $CH_2CH_3$, or $CH(CH_3)_2$;
$R^{2a}$ is F, Cl, Br, I, H, $CH_3$, $CH_2CH_3$, $CH(CH_3)_2$, OH, $OCH_3$, $OCH_2OCH_3$, or $OCH(CH_3)_2$;
$R^{2b}$ is H, $CH_3$, $CH_2CH_3$, $CH(CH_3)_2$, OH, $OCH_3$, $OCH_2OCH_3$, or $OCH(CH_3)_2$;
$R^{2c}$ is H, $CH_3$, $CH_2CH_3$, $CH(CH_3)_2$, OH, $OCH_3$, $OCH_2OCH_3$, or $OCH(CH_3)_2$;
$R^{2d}$ is H, $CH_3$, $CH_2CH_3$, $CH(CH_3)_2$, OH, $OCH_3$, $OCH_2OCH_3$, or $OCH(CH_3)_2$;
$R^{x2c}$ is H, $CH_3$, $CH_2CH_3$, $CH(CH_3)_2$, OH, $OCH_3$, $OCH_2OCH_3$, or $OCH(CH_3)_2$; and
$R^{x2a}$ is H, $CH_3$, $CH_2CH_3$, or $CH(CH_3)_2$.

5. The method of claim 1, wherein the compound has the formula:

6. The method of claim 5, wherein $R^{x1a}$ and $R^{x2a}$ are both H.

7. The method of claim 6, wherein the compound has the formula:

8. The method of claim 6, wherein the compound has the formula:

* * * * *